United States Patent [19]
Humbert-Droz et al.

[11] Patent Number: 6,083,531
[45] Date of Patent: Jul. 4, 2000

[54] FAST DISINTEGRATING ORAL DOSAGE FORM

[75] Inventors: Pierre Humbert-Droz, Collex-Bossy; Matthias Seidel, Gland, both of Switzerland; Rosa Martani, Divonne-les-Bains, France

[73] Assignee: Novartis Consumer Health S.A., Nyon, Switzerland

[21] Appl. No.: 09/155,882

[22] PCT Filed: Apr. 4, 1997

[86] PCT No.: PCT/EP97/01696

§ 371 Date: Oct. 7, 1998

§ 102(e) Date: Oct. 7, 1998

[87] PCT Pub. No.: WO97/38679

PCT Pub. Date: Oct. 23, 1997

[30] Foreign Application Priority Data

Apr. 16, 1996 [DE] Germany ............................ 96810236

[51] Int. Cl.⁷ ............................................. A61K 9/20
[52] U.S. Cl. ..................... 424/464; 424/435; 424/439; 424/441; 514/770; 514/772.3; 514/777; 514/778; 514/779; 514/781; 514/782
[58] Field of Search ....................... 424/439, 440, 424/441, 464, 465, 435

[56] References Cited

U.S. PATENT DOCUMENTS

| | | | |
|---|---|---|---|
| 2,887,437 | 5/1959 | Klioze et al. ............................ | 167/81 |
| 4,684,534 | 8/1987 | Valentine ................................. | 427/3 |
| 4,866,046 | 9/1989 | Amer ...................................... | 514/159 |
| 4,886,669 | 12/1989 | Ventouras .............................. | 424/469 |
| 5,178,878 | 1/1993 | Wehling et al. ........................ | 424/366 |
| 5,225,197 | 7/1993 | Bolt et al. .............................. | 424/440 |
| 5,330,760 | 7/1994 | Walton . | |
| 5,464,632 | 11/1995 | Cousin et al. .......................... | 424/465 |
| 5,466,464 | 11/1995 | Masaki et al. ......................... | 424/434 |
| 5,543,153 | 8/1996 | Walton .................................... | 424/466 |
| 5,567,439 | 10/1996 | Myers et al. ........................... | 424/486 |
| 5,595,761 | 1/1997 | Allen et al. ............................ | 424/484 |

FOREIGN PATENT DOCUMENTS

| | | |
|---|---|---|
| 2061917 | 8/1993 | Canada . |
| 0 313 328 | 4/1989 | European Pat. Off. . |
| 0627218 | 12/1994 | European Pat. Off. . |
| 0651997 | 5/1995 | European Pat. Off. . |
| 91 04018 | 4/1991 | WIPO . |
| 91 04757 | 4/1991 | WIPO . |
| 92 15204 | 9/1992 | WIPO . |
| 9520377 | 8/1995 | WIPO . |
| 9520953 | 8/1995 | WIPO . |
| 9534290 | 12/1995 | WIPO . |

*Primary Examiner*—James M. Spear
*Attorney, Agent, or Firm*—Michael P. Morris; John D. Thallemer

[57] ABSTRACT

The present invention relates to a solid pharmaceutical dosage form for oral administration, consisting essentially of
(a) at least one active substance,
(b) at least one filler,
(c) at least one binding agent, and
(d) optionally usual auxiliaries, which dosage form, however, does not contain agar;

which dosage form is manufactured without applying any compression force to the mixture of the components (a), (b), (c) and (d); and which dosage form disintegrates when taken into the mouth within 15 seconds.

19 Claims, No Drawings

FAST DISINTEGRATING ORAL DOSAGE FORM

This application is a 371 of PCT/EP97/01696 filed Apr. 4, 1997.

The present invention relates to the field of pharmaceutical orally ingested solid dosage forms, which are designed to dissolve rapidly within the mouth. Currently two main technologies are used to obtain such type of dosage forms: (1) The active ingredient is mixed with water-soluble diluents and compressed on a tableting machine at low to medium compression force. This is the more conventional approach. (2) A suspension is prepared with the active ingredient and appropriate excipients. The suspension is dispensed into blister packs and freeze-dried.

Many people are unwilling and/or unable to swallow tablets, capsules or traditional solid dosage forms. One approach suitable for these persons is the use of effervescent tablets or granules. However, the use of effervescent tablets requires preparatory steps before administration of the drug and the presence of water and a suitable mixing container. In addition, the manufacture and stability of effervescent tablets is often problematic. Another possibility is the use of a chewing gum or chewing tablet containing a medicament capable of absorption through the buccal cavity. Substantial disadvantages inherent in such a delivery system are that many medicaments are not suited for buccal absorption and that many persons are not able to chew gums or tablets because of braces, dental work etc. Furthermore, gums are often difficult to prepare.

A more recent approach is the OraSolv® technology of the company Cima. Orasolv® is an oral dosage form, which involves incorporating microencapsulated drug ingredients into a tablet that dissolves in the mouth without the need for chewing or water. The Orasolv® tablets are obtained by compression and packed into special peel-off blister packs because their mechanical resistance is insufficient in normal blister packs. The OraSolv® tablets normally need 15 to 60 seconds to dissolve in the mouth, which is longer than ideally aspired to in modern fast melting oral dosage forms. The same disadvantage of dissolving not rapidly enough in the mouth is common with many other approaches to fast melting oral dosage forms.

A fast dissolving (normally in 3 to 5 seconds) oral drug delivery system named Zydis® is known from the company R.P. Scherer. The principle of this technology consists in preparing an aqueous suspension of the active ingredient and the excipients, which is dispensed into blister packs and the water removed by a freeze drying process. The final product is obtained by sealing the dried product in special peel-off blister packs—like Orasolv® due to lacking mechanical resistance in normal blister packs. A major disadvantage of this technology is the time-consuming and costly freeze-drying process. Furthermore, the effectiveness of a freeze-drying process always depends on the physico-chemical parameters of the active substances used. For certain active substances, especially such having a high solubility in water, it is therefore difficult or impossible to apply a freeze-drying process and consequently this technology. Finally, the development of units with high doses (up to 500 mg or even 1000 mg) of active ingredients and/or combinations of active ingredients is difficult or impossible, respectively with this technology.

The present invention addresses the needs mentioned above and the problems encountered with currently available technologies. The expensive freeze-drying process is avoided. The manufacture of the dosage form of the invention is simple and suitable for a broad range of active ingredients with different physico-chemical parameters, for high dose unit forms (up to e.g. 1000 mg, in particular 500 mg, of active substance) and also for combinations of active ingredients.

The present invention provides a solid pharmaceutical dosage form adapted for direct oral administration, i.e. for direct insertion into the mouth of a patient. This is particularly useful in administration of medicaments to individuals who cannot or will not chew, such as debilitated patients, patients who have difficulty swallowing solids and the elderly.

Therefore, the present invention relates to a solid pharmaceutical dosage form for oral administration, consisting essentially of (a) at least one active substance,
(b) at least one filler,
(c) at least one binding agent, and
(d) optionally usual auxiliaries, which dosage form disintegrates when taken into the mouth within 15 seconds, preferably within 10 seconds, and especially within 5 seconds.

More precisely, the solid pharmaceutical dosage form consists essentially of a mixture, especially a homogeneous mixture, of the components (e), (b), (c) and (d) mentione above.

Active substances are especially pharmaceuticals but may be also, for example, vitamins, minerals or dietary supplements. Pharmaceuticals may include, without limitation, antacids, analgesics, anti-inflammatories, antibiotics, laxatives, anorexics, antiasthmatics, antidiuretics, antiflatulents, antimigraine agents, antispasmodics, sedatives, antihyperactives, tranquilizers, antihistamines, decongestants, betablockers, hormones and combinations thereof. Preferred active substances are analgesics and non-steroidal anti-inflammatory drugs, such as diclofenac, ketoprofen, ibuprofen, aspirin or paracetamol or a pharmaceutically acceptable salt thereof, and hormones, e.g. melatonin. Especially preferred is diclofenac which may be present either as free acid or as a pharmaceutically acceptable salt thereof, e.g. the potassium or sodium salt.

The filler can be chosen from those known in the art including mannitol, lactose, calcium hosphates, calcium sulphates, sucrose, glucose, fructose, sorbitol and xylitol. It has been found that a particularly advantageous filler is mannitol, because it is particularly useful in forming the low density matrix of the dosage form that disintegrates rapidly within the mouth. Furthermore, mannitol permits an easy drying process of the formulation after filling the suspension/solution into the blisters because of its non-hygroscopic character. The filler is usually present in an amount of at least 50 weight-%, preferably at least 60 weight-%, and especially at least 70 weight-% of the total dosage form.

The binding agent (or binder) is primarily used to give sufficient consistency to the formulation to avoid breaking of the article when removed from the blisters and during handling. Binding agents that can be used include polyethylene glycols, acacia, tragacanth, starch, cellulose materials, polyvinylpyrrolidones, alginic acid or a salt or an ester thereof, carrageenan gum, xanthan gum, gellan gum and the like. Also gelatin comes into consideration as a binder.

Preferred as binding agents are polyethylene glycols, carrageenan gum, xanthan gum, gellan gum, starch, cellulose materials, polyvinyl pyrrolidones, alginic acid or a salt or an ester thereof, and also gelatin.

Especially preferred are polyethylene glycols and polyvinylpyrrolidones. In particular, polyethylene glycol, e.g.

polyethylene glycol 6000, is used. The binding agent is usually present in an amount of from 0.1 up to 10 weight-% and especially of from 0.2 up to 3 weight-% of the total dosage form.

Covered by the term "usual auxiliaries" are, for example, lubricants. They are primarily used to avoid sticking of the dried product to the surface of the mould. Examples of lubricants which can be used are talc, magnesium stearate or calcium stearate, stearic acid, polyethyleneglycols, sodium stearyl fumarate, hydrogenated vegetable oil, a behenic acid derivative and the like. It has been found that talc, hydrogenated vegetable oil and a behenic acid derivative—in particular talc—are especially useful lubricants in the dosage forms of the present invention. A behenic acid derivative is e.g. glyceryl behenate (also called "tribehenin") which corresponds to a mixture of glycerides (mainly triglycerides) of fatty acids (mainly behenic acid). Corresponding products on the market include the Compritol® series of the company Gattefossé (France). If used, the lubricant is usually present in an amount of up to 15 weight-%, e.g. in an amount of from 1 up to 15 weight %, and especially in an amount of up to 10 weight-% of the total dosage form.

The dosage forms of the present invention may include further auxiliaries (adjuvants) known in the art including flavors, aromas, sweeteners, colorants, buffering agents, acidifying agents, diluents, preservatives and the like.

The present invention further relates to a process for preparing the solid pharmaceutical dosage form for oral administration of the invention, which process comprises (A) preparing a suspension or solution which contains alit the components (a), (b), (c) and (d) of the dosage form,
(B) dispensing the suspension or solution into moulds, corresponding in size and shape to that of the pharmaceutical dosage form,
(C) removing the solvent without applying a freeze-drying process, and
(D) removing the dried units for storage in suitable containers or sealing them directly in the moulds.

Thus, the manufacture of the dosage form according to the present invention includes preparing a suspension (or solution), where the active ingredient is dispersed or dissolved in a solvent together with all the other components of the composition, such as fillers, binders and the usual auxiliaries present. The solvent is e.g. water, or a mixture of water with a co-solvent, e.g. ethanol, or even a pure non-aqueous solvent, e.g. ethanol. The active ingredient is normally used as the pure substance in different crystalline forms but it can also be e.g. microencapsulated. After preparation of the suspension (or solution), the latter is dispensed into moulds, e.g. blisters. This may be done either manually, semi-automatically or automatically.

Surprisingly, it is possible to dry the moulds, e.g. blisters,—that is to remove the solvent(s)—without applying a freeze-drying process, as known e.g. from the Zydise® technology of the prior art. This can be done, for example, by simple storage at room temperature or at elevated temperatures, or by storage at room temperature or at elevated temperatures under reduced pressure, or by applying microwave radiation, or by applying microwave radiation under reduced pressure. The evaporation normally is done at a temperature of from 10 up to 80° C., e.g. at room temperature between 15 and 25° C., or by heating up to 80° C., especially up to 50° C. "Under reduced pressure" preferably means pressures of from 0.1 mbar up to 200 mbar, but also high vacuum, e.g. 0.001 to 0.1 mbar, is possible. When microwave radiation is applied, this is preferably done in a system that is able to work on-line (continuously) during the manufacturing process. The process is simple and suitable for a broad range of active ingredients with different physico-chemical parameters, for high dose unit forms (up to 1000 mg, in particular 500 mg of active substance) and also for combinations of active ingredients.

From the above-said it has become clear that the dosage form of the present invention is manufactured without applying any compression force to the mixture of the components (a), (b), (c) and (d). As a result of the particular process of manufacture used, the dosage form of the invention normally has a density of 200–1000 mg/ml, preferably 300–900 mg/ml, more preferably 600–900 mg/ml, or 400–800 mg/ml. This is a density that is much lower than that of compressed dosage forms like normal tablets etc. (having densities of above 1000 mg/ml). As a result of its unusually low density, the dosage form of the invention disintegrates more rapidly than would be the case, if the mixture of its components (a), (b), (c) and (d) are subjected to compression force.

The dried units may e.g. be sealed or removed from the moulds for storage in suitable containers. According to a preferred embodiment of the invention, the dried blisters are finally sealed to obtain the finished product, either in special peel-off blister packs or, preferably, in normal blister packs.

The dosage form is presented e.g. as a tablet of a size and shape adapted for direct oral administration to a patient. The tablet is pleasant to take and, once placed into the mouth, will disintegrate substantially and instantly without any voluntary action by the patient, e.g. chewing. Upon disintegration of the tablet, the active ingredient is released and can be swallowed as a suspension or absorbed from the buccal cavity. Buccal absorption can be particularly advantageous for substances submitted to a high first hepatic metabolism.

The dosage form according to the present invention is convenient to use for the consumer without the need of water or additional devices. Moreover, the instant disintegration and/or dissolution gives a sensation of a rapid and powerful action of the pharmaceutical dosage form and makes it unique and motivating for the patient to take.

An oral dosage form according to the present invention may also be, for example, a shaped article. The mass of each such an article is generally less than about 2.0 g. Preferably, the articles are circular, disk-like with a diameter between 5 and 20 mm.

The following examples illustrate the invention.

EXAMPLE 1

Fast Melting Oral Dosage Form Containing 12.5 mg of Diclofenac Potassium
(overall weight: 200 mg)

| Compositon | mg/unit |
| --- | --- |
| Diclofenac potassium | 12.5 |
| Mannitol | 152.3 |
| Polyethylene glycol 6000 | 1.6 |
| Citric acid | 10.0 |
| Talc | 16.0 |
| Aspartam | 6.0 |
| Lemon aroma | 1.6 |
| Purified water | 150.0 |

Diclofenac potassium, mannitol, talc, aspartam and the aroma are mixed for 5 min, sifted through a 0.5 mm mesh screen and then mixed again for 15 min. Citric acid and polyethylene glycol are dissolved in purified water. The former dry mixture containing diclofenac potassium etc. is suspended in the latter aqueous solution under stirring. While stirring, adequate aliquots of the suspension are dispensed manually with a pipette in blisters, and the blisters are dried at room temperature for 10 h. The dried units may now be removed from the blisters and stored in glass containers. Alternatively, the dried blisters may be sealed to obtain the finished product.

In an analogous manner as described in example 1, also the fast melting oral dosage forms of examples 2 to 5 are manufactured.

EXAMPLE 2

Fast Melting Oral Dosage Form Containing 12.5 mg of Diclofenac potassium (overall weight: 200,4 mg)

| Compositon | mg/unit |
|---|---|
| Diclofenac potassium | 12.5 |
| Mannitol | 152.3 |
| Polyvinylpyrrolidone | 2.0 |
| Citric acid | 10.0 |
| Talc | 16.0 |
| Aspartam | 6.0 |
| Lemon aroma | 1.6 |
| Purified water | 150.0 |

EXAMPLE 3

Fast Melting Oral Dosage Form Containing 12.5 mg of Ketoprofen (overall weight: 190 mg)

| Compositon | mg/unit |
|---|---|
| Ketoprofen | 12.5 |
| Mannitol | 152.3 |
| Polyethylene glycol | 1.6 |
| Talc | 16.0 |
| Aspartam | 6.0 |
| Mint aroma | 1.6 |
| Purified water | 150.0 |

EXAMPLE 4

Fast Melting Oral Dosage Form Containing 3.0 mg of Melatonin (overall weight: 190 mg)

| Compositon | mg/unit |
|---|---|
| Melatonin | 3.0 |
| Mannitol | 161.8 |
| Polyethylene glycol | 1.6 |
| Talc | 16.0 |
| Aspartam | 6.0 |
| Mint aroma | 1.6 |
| Purified water | 150.0 |

EXAMPLE 5

Fast Melting Oral Dosage Form Containing 12.5 mg Diclofenac Potassium (overall weight: 400 mg)

| Compositon | (mg/unit) |
|---|---|
| Diclofenac potassium | 12.5 |
| Mannitol | 353.5 |
| Gellan gum | 2 |
| Polyethylene glycol | 8 |
| Talc | 16 |
| Aspartam | 6 |
| Mint aroma | 2 |
| Purified water | 37.5 |
| ethanol | 75 |

In this example—contrary to example 1—the drying of the blisters is done at 50° C. under reduced pressure (0.1 mbar). Finally, the dried blisters are sealed to obtain the finished product.

What is claimed is:

1. A solid pharmaceutical dosage form for oral administration, consisting essentially of a mixture of
   (a) at least one active substance,
   (b) at least one filler,
   (c) at least one binding agent, and
   (d) optionally usual auxiliaries,
   which dosage form, however, does not contain agar which dosage form has a density of 200–1000 mg./ml.;
   which dosage form is manufactured without applying any compression force to the mixture of the components (a), (b), (c) and (d); and
   which dosage form disintegrates when taken into the mouth within 15 seconds.

2. The solid pharmaceutical dosage form according to claim 1 wherein
   at least one filler is selected from the group consisting of mannitol, lactose, calcium phosphates, calcium sulphates, sucrose, glucose, fructose, sorbitol and xylitol, and
   at least one binding agent is selected from the group consisting of polyethylene glycols, acacia, tragacanth, starch, cellulose materials, polyvinylpyrrolidones, alginic acid or a salt or an ester thereof, carrageenan gum, xanthan gum, gellan gum and gelatin.

3. The solid pharmaceutical dosage form according to claim 1, which dosage form has a density of 300–900 mg/ml.

4. The solid pharmaceutical dosage form according to claim 2, which dosage form has a density of 300–900 mg/ml.

5. The solid pharmaceutical dosage form according to claim 3, which dosage form is prepared from a homogeneous suspension or solution that contains all the components (a), (b), (c) and (d) of the dosage form.

6. The solid pharmaceutical dosage form according to claim 4, which dosage form is prepared from a homogeneous suspension or solution that contains all the components (a), (b), (c) and (d) of the dosage form.

7. The solid pharmaceutical dosage form according to claim 2, wherein the filler (b) is present in an amount of at least 70 weight-% of the total dosage form, and the binding agent (c) is present in an amount of from 0.2 up to 3 weight-% of the total dosage form.

8. The solid pharmaceutical dosage form according to claim 3, wherein the filler (b) is present in an amount of at least 70 weight-% of the total dosage form, and the binding agent (c) is present in an amount of from 0.2 up to 3 weight-% of the total dosage form.

9. The solid pharmaceutical dosage form according to claim 2 wherein
at least one binding agent is selected from the group consisting of polyethylene glycols, acacia, tragacanth, starch, cellulose materials, polyvinylpyrrolidones and alginic acids.

10. The solid pharmaceutical dosage form according to claim 2 wherein
at least one filler is mannitol, and
at least one binding agent is selected from the group consisting of polyethylene glycols, polyvinylpyrrolidones, carrageenan gum, xanthan gum and gellan gum.

11. The solid pharmaceutical dosage form according to claim 1, wherein the filler (b) is present in an amount of at least 50 weight-percent of the total dosage form, and the binding agent (c) is present in an amount of from 0.1 up to 10 weight-percent of the total dosage form.

12. The solid pharmaceutical dosage form according to claim 1, wherein the composition comprises as usual auxiliaries (d) at least one lubricant.

13. The solid pharmaceutical dosage form according to claim 12, wherein the lubricant is selected from the group consisting of talc, hydrogenated vegetable oil and a behenic acid derivative, and combinations thereof.

14. The solid pharmaceutical dosage form for oral administration according to claim 12, wherein the lubricant comprises talc.

15. The solid pharmaceutical dosage form according to claim 1, wherein the active substance is selected from the group consisting of diclofenac, ketoprofen, ibuprofen, aspirin, paracetamol, melatonin, and pharmaceutically acceptable salts thereof.

16. A process for preparing a solid pharmaceutical dosage form for oral administration, the process comprising:

(A) preparing a suspension of solution, said suspension or solution comprising
(1) at least one active substance,
(2) at least one filler,
(3) at least one binding agent,
(4) optionally usual excipients; and
(5) a solvent,
said suspension or solution, however, not comprising agar;

(B) dispensing the suspension or solution into molds, corresponding in size and shape to that of the pharmaceutical dosage form.

(C) removing the solvent without applying a freeze-drying process, thereby producing dried units of the solid pharmaceutical dosage form having a density of 200–1000 mg./ml.; and (D) either removing the dried units for storage from the molds for storage in suitable containers, or, sealing the dried units directly into the molds.

17. The process of claim 16, wherein step (C) is accomplished either by evaporating the solvent at a temperature of from 10 up to 80° C., optionally under reduced pressure, or by applying microwave radiation, optionally under reduced pressure.

18. The process of claim 16, in which the solvent used for the preparation of the suspension or solution under (A) is selected from the group consisting of water, a mixture of water and ethanol, or ethanol.

19. The process of claim 18, in which the solvent used for the preparation of the suspension or solution under (A) is a mixture of water and ethanol.

* * * * *